US010349948B2

(12) United States Patent
Rogowski et al.

(10) Patent No.: US 10,349,948 B2
(45) Date of Patent: Jul. 16, 2019

(54) LEFT ATRIAL APPENDAGE OCCLUSION DEVICE

(71) Applicant: Jitmed Sp. z o.o., Gdynia (PL)

(72) Inventors: Jan Rogowski, Tczew (PL); Maciej Brzezinski, Gdansk (PL); Leszek Dabrowski, Gdansk (PL)

(73) Assignee: JITMED SP. Z. O.O. (PL)

( * ) Notice: Subject to any disclaimer, the term of this patent is extended or adjusted under 35 U.S.C. 154(b) by 277 days.

(21) Appl. No.: 15/300,140

(22) PCT Filed: Mar. 31, 2014

(86) PCT No.: PCT/PL2014/000031
§ 371 (c)(1),
(2) Date: Sep. 28, 2016

(87) PCT Pub. No.: WO2015/152741
PCT Pub. Date: Oct. 8, 2015

(65) Prior Publication Data
US 2017/0135700 A1 May 18, 2017

(51) Int. Cl.
*A61B 17/08* (2006.01)
*A61B 17/122* (2006.01)
(Continued)

(52) U.S. Cl.
CPC .... *A61B 17/1227* (2013.01); *A61B 17/00234* (2013.01); *A61B 17/1285* (2013.01); *A61B 2017/00243* (2013.01)

(58) Field of Classification Search
CPC . A61B 17/44; A61B 17/1227; A61B 17/1285; A61B 17/00234;
(Continued)

(56) References Cited

U.S. PATENT DOCUMENTS 6,152,144 A 11/2000 Lesh et al.
6,652,555 B1 11/2003 Van Tassel et al.
(Continued)

FOREIGN PATENT DOCUMENTS

EP 1433437 A2 6/2004
WO 2007/009099 A2 1/2007
(Continued)

OTHER PUBLICATIONS

International Search Report and Written Opinion for Application No. PCT/PL2014/000031 dated Jan. 29, 2015.

*Primary Examiner* — Vi X Nguyen
(74) *Attorney, Agent, or Firm* — Ostrolenk Faber LLP

(57) ABSTRACT

A left atrial appendage closure device that includes two clamping jaws (2) fixed to a bow (3) having a flange with a cut slot, where each of the edges of the slot is connected with a clamping jaw (2). The jaws (2) contain internal channels (5). In a section perpendicular to the symmetry axes of the internal channels (5), a line (a) connecting the symmetry axes of the internal channels (5) is distant from an imaginary line (b) connecting the centers of sections of the bow (3) arms by a distance (14). The bow (3) has in the central part of its periphery a larger section (6) than a section (7) in the places where the bow (3) arms are connected with the jaws (2). The jaw (2) wall (9) from the adjacent jaw (2) side is the thinnest, whereas the wall (9) from the side of fixing the clamping jaw (2) to the bow (3) is the thickest.

8 Claims, 4 Drawing Sheets

(51) Int. Cl.
*A61B 17/128* (2006.01)
*A61B 17/00* (2006.01)

(58) Field of Classification Search
CPC .......... A61B 2017/00243; A61B 17/08; A61B 17/122; A61B 17/128
See application file for complete search history.

(56) References Cited

U.S. PATENT DOCUMENTS

| | | |
|---|---|---|
| 6,652,556 B1 | 11/2003 | VanTassel et al. |
| 6,666,861 B1 | 12/2003 | Grabek |
| 6,689,150 B1 | 2/2004 | VanTassel et al. |
| 6,941,169 B2 | 9/2005 | Pappu |
| 6,994,092 B2 | 2/2006 | van der Burg et al. |
| 7,044,134 B2 | 5/2006 | Khairkhahan et al. |
| 7,128,073 B1 | 10/2006 | van der Burg et al. |
| 7,152,605 B2 | 12/2006 | Khairkhahan et al. |
| 7,192,439 B2 | 3/2007 | Khairkhahan et al. |
| 7,527,634 B2 | 5/2009 | Zenati et al. |
| 7,549,983 B2 | 6/2009 | Roue et al. |
| 7,566,336 B2 | 7/2009 | Corcoran et al. |
| 7,597,704 B2 | 10/2009 | Frazier et al. |
| 7,713,282 B2 | 5/2010 | Frazier et al. |
| 7,722,641 B2 | 5/2010 | van der Burg et al. |
| 7,727,189 B2 | 6/2010 | VanTassel et al. |
| 7,735,493 B2 | 6/2010 | van der Burg et al. |
| 7,806,846 B2 | 10/2010 | Chanduszko et al. |
| 7,824,397 B2 | 11/2010 | McAuley |
| 7,828,810 B2 | 11/2010 | Liddicoat et al. |
| 7,846,168 B2 | 12/2010 | Liddicoat et al. |
| 7,918,865 B2 | 4/2011 | Liddicoat et al. |
| 7,972,359 B2 | 7/2011 | Kreidler |
| 7,992,757 B2 | 8/2011 | Wheeler et al. |
| 7,998,138 B2 | 8/2011 | McAuley |
| 8,007,504 B2 | 8/2011 | Zenati et al. |
| 8,043,329 B2 | 10/2011 | Khairkhahan et al. |
| 8,080,032 B2 | 12/2011 | van der Burg et al. |
| 8,097,015 B2 | 1/2012 | Devellian |
| 8,142,470 B2 | 3/2012 | Quinn et al. |
| 8,262,694 B2 | 9/2012 | Widomski et al. |
| 8,287,563 B2 | 10/2012 | Khairkhahan et al. |
| 8,323,309 B2 | 12/2012 | Khairkhahan et al. |
| 8,361,111 B2 | 1/2013 | Widomski et al. |
| 8,460,282 B2 | 6/2013 | McAuley |
| 8,498,691 B2 | 7/2013 | Moll et al. |
| 8,535,343 B2 | 9/2013 | van der Burg et al. |
| 8,561,872 B2 | 10/2013 | Wheeler et al. |
| 8,636,764 B2 | 1/2014 | Miles et al. |
| 8,647,367 B2 | 2/2014 | Kassab et al. |
| 8,663,245 B2 | 3/2014 | Francischelli et al. |
| 8,663,268 B2 | 3/2014 | Quinn et al. |
| 8,663,273 B2 | 3/2014 | Khairkhahan et al. |
| 8,685,055 B2 | 4/2014 | VanTassel et al. |
| 8,690,911 B2 | 4/2014 | Miles et al. |
| 8,715,302 B2 | 5/2014 | Ibrahim et al. |
| 8,715,318 B2 | 5/2014 | Miles et al. |
| 8,721,663 B2 | 5/2014 | Kaplan et al. |
| 8,740,934 B2 | 6/2014 | McGuckin, Jr. |
| 8,764,793 B2 | 7/2014 | Lee |
| 8,771,297 B2 | 7/2014 | Miller et al. |
| 8,784,469 B2 | 7/2014 | Kassab |
| 8,795,297 B2 | 8/2014 | Liddicoat et al. |
| 8,795,310 B2 | 8/2014 | Fung et al. |
| 8,795,328 B2 | 8/2014 | Miles et al. |
| 8,801,746 B1 | 8/2014 | Kreidler et al. |
| 8,828,051 B2 | 9/2014 | Javois et al. |
| 8,834,519 B2 | 9/2014 | van der Burg et al. |
| 8,840,641 B2 | 9/2014 | Miles et al. |
| 8,845,711 B2 | 9/2014 | Miles et al. |
| 8,932,308 B2 | 1/2015 | Ibrahim et al. |
| 8,974,473 B2 | 3/2015 | Kaplan et al. |
| 8,986,325 B2 | 3/2015 | Miller et al. |
| 9,011,551 B2 | 4/2015 | Oral et al. |
| 9,014,449 B2 | 4/2015 | Zhong et al. |
| 9,089,414 B2 | 7/2015 | Zimmerman et al. |
| 9,132,000 B2 | 9/2015 | VanTassel et al. |
| 9,144,431 B2 | 9/2015 | Friedman et al. |
| 9,168,043 B2 | 10/2015 | van der Burg et al. |
| 9,186,152 B2 | 11/2015 | Campbell et al. |
| 9,186,174 B2 | 11/2015 | Krishnan |
| 9,198,683 B2 | 12/2015 | Friedman et al. |
| 9,211,124 B2 | 12/2015 | Campbell et al. |
| 9,220,402 B2 | 12/2015 | Rothe et al. |
| 9,271,819 B2 | 3/2016 | Liddicoat et al. |
| 9,314,249 B2 | 4/2016 | Kreidler et al. |
| 9,351,716 B2 | 5/2016 | Miles et al. |
| 9,375,218 B2 | 6/2016 | Wheeler et al. |
| 9,408,608 B2 | 8/2016 | Clark, III et al. |
| 9,421,004 B2 | 8/2016 | Roue et al. |
| 9,427,235 B2 | 8/2016 | Krishnan |
| 9,445,895 B2 | 9/2016 | Kreidler |
| 2002/0111647 A1 | 8/2002 | Khairkhahan et al. |
| 2002/0183823 A1 | 12/2002 | Pappu |
| 2003/0181942 A1 | 9/2003 | Sutton et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0208231 A1* | 11/2003 | Williamson, IV .......... A61B 17/00234 606/205 |
| 2003/0212432 A1 | 11/2003 | Khairkhahan et al. |
| 2003/0220667 A1 | 11/2003 | van der Burg et al. |
| 2004/0030335 A1 | 2/2004 | Zenati et al. |
| 2004/0034366 A1 | 2/2004 | van der Burg et al. |
| 2004/0044361 A1 | 3/2004 | Frazier et al. |
| 2004/0064138 A1 | 4/2004 | Grabek |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0215230 A1 | 10/2004 | Frazier et al. |
| 2004/0230222 A1 | 11/2004 | van der Burg et al. |
| 2005/0004641 A1 | 1/2005 | Pappu |
| 2005/0004652 A1 | 1/2005 | van der Burg et al. |
| 2005/0038470 A1 | 2/2005 | van der Burg et al. |
| 2005/0070952 A1 | 3/2005 | Devellian |
| 2005/0113861 A1 | 5/2005 | Corcoran et al. |
| 2005/0154404 A1 | 7/2005 | Liddicoat et al. |
| 2005/0177182 A1 | 8/2005 | van der Burg et al. |
| 2005/0192626 A1 | 9/2005 | Widomski et al. |
| 2005/0203568 A1 | 9/2005 | Burg et al. |
| 2005/0209636 A1 | 9/2005 | Widomski et al. |
| 2005/0216054 A1 | 9/2005 | Widomski et al. |
| 2005/0222533 A1 | 10/2005 | Chanduszko et al. |
| 2005/0234540 A1 | 10/2005 | Peavey et al. |
| 2005/0234543 A1 | 10/2005 | Glaser et al. |
| 2006/0020271 A1 | 1/2006 | Stewart et al. |
| 2006/0206148 A1 | 9/2006 | Khairkhahan et al. |
| 2006/0247680 A1 | 11/2006 | Amplatz et al. |
| 2006/0253129 A1 | 11/2006 | Liddicoat et al. |
| 2007/0043344 A1 | 2/2007 | McAuley |
| 2007/0060951 A1 | 3/2007 | Shannon |
| 2007/0066993 A1 | 3/2007 | Kreidler |
| 2007/0073313 A1 | 3/2007 | Liddicoat et al. |
| 2007/0083227 A1 | 4/2007 | van der Burg et al. |
| 2007/0083230 A1 | 4/2007 | Javois |
| 2007/0149995 A1 | 6/2007 | Quinn et al. |
| 2007/0156123 A1 | 7/2007 | Moll et al. |
| 2007/0260278 A1 | 11/2007 | Wheeler et al. |
| 2007/0270891 A1 | 11/2007 | McGuckin |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0147097 A1 | 6/2008 | Liddicoat et al. |
| 2008/0221593 A1 | 9/2008 | Liddicoat et al. |
| 2008/0243183 A1 | 10/2008 | Miller et al. |
| 2009/0039879 A1 | 2/2009 | Dieny |
| 2009/0082623 A1 | 3/2009 | Rothe et al. |
| 2009/0099596 A1 | 4/2009 | McGuckin, Jr. et al. |
| 2009/0112249 A1 | 4/2009 | Miles et al. |
| 2009/0143791 A1 | 6/2009 | Miller et al. |
| 2009/0157118 A1 | 6/2009 | Miller et al. |
| 2009/0171386 A1 | 7/2009 | Amplatz et al. |
| 2009/0182326 A1 | 7/2009 | Zenati et al. |
| 2009/0306685 A1 | 12/2009 | Fill |

(56) References Cited

U.S. PATENT DOCUMENTS

| | | |
|---|---|---|
| 2010/0114152 A1 | 5/2010 | Shukla |
| 2010/0191279 A1 | 7/2010 | Kassab et al. |
| 2010/0204716 A1 | 8/2010 | Stewart et al. |
| 2010/0228279 A1 | 9/2010 | Miles et al. |
| 2010/0228285 A1 | 9/2010 | Miles et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0009853 A1 | 1/2011 | Bertolero et al. |
| 2011/0022079 A1 | 1/2011 | Miles et al. |
| 2011/0046622 A1 | 2/2011 | McAuley |
| 2011/0054515 A1 | 3/2011 | Bridgeman et al. |
| 2011/0082495 A1 | 4/2011 | Ruiz |
| 2011/0144660 A1 | 6/2011 | Liddicoat et al. |
| 2011/0208233 A1 | 8/2011 | McGuckin, Jr. et al. |
| 2011/0218566 A1 | 9/2011 | van der Burg et al. |
| 2011/0270303 A1 | 11/2011 | Wheeler et al. |
| 2011/0276075 A1 | 11/2011 | Fung et al. |
| 2011/0282250 A1 | 11/2011 | Fung et al. |
| 2011/0295060 A1 | 12/2011 | Zenati et al. |
| 2011/0301595 A1 | 12/2011 | McAuley |
| 2012/0035643 A1 | 2/2012 | Khairkhahan et al. |
| 2012/0065662 A1 | 3/2012 | van der Burg et al. |
| 2012/0065667 A1 | 3/2012 | Javois et al. |
| 2012/0116269 A1 | 5/2012 | McAuley |
| 2012/0157916 A1 | 6/2012 | Quinn et al. |
| 2012/0172927 A1 | 7/2012 | Campbell et al. |
| 2012/0221042 A1 | 8/2012 | Schwartz et al. |
| 2012/0239083 A1 | 9/2012 | Kreidler |
| 2012/0316584 A1 | 12/2012 | Miles et al. |
| 2012/0323262 A1 | 12/2012 | Ibrahim et al. |
| 2012/0323270 A1 | 12/2012 | Lee |
| 2012/0330351 A1 | 12/2012 | Friedman et al. |
| 2013/0006343 A1 | 1/2013 | Kassab |
| 2013/0012982 A1 | 1/2013 | Khairkhahan et al. |
| 2013/0018413 A1 | 1/2013 | Oral et al. |
| 2013/0018414 A1 | 1/2013 | Widomski et al. |
| 2013/0083983 A1 | 4/2013 | Zhong et al. |
| 2013/0110154 A1 | 5/2013 | van der Burg et al. |
| 2013/0138138 A1 | 5/2013 | Clark et al. |
| 2013/0144311 A1 | 6/2013 | Fung et al. |
| 2013/0165965 A1 | 6/2013 | Carlson et al. |
| 2013/0165966 A1 | 6/2013 | Widomski et al. |
| 2013/0178889 A1 | 7/2013 | Miles et al. |
| 2013/0190799 A1 | 7/2013 | Clark |
| 2013/0218192 A1 | 8/2013 | Erzberger et al. |
| 2013/0218193 A1 | 8/2013 | Erzberger et al. |
| 2013/0237908 A1 | 9/2013 | Clark |
| 2013/0245369 A1 | 9/2013 | Dal Molin |
| 2013/0331884 A1 | 12/2013 | Van der Burg et al. |
| 2013/0338686 A1 | 12/2013 | Ruiz |
| 2014/0005714 A1 | 1/2014 | Quick et al. |
| 2014/0058371 A1 | 2/2014 | Krishnan |
| 2014/0100596 A1 | 4/2014 | Rudman et al. |
| 2014/0142612 A1 | 5/2014 | Li et al. |
| 2014/0148842 A1 | 5/2014 | Khairkhahan et al. |
| 2014/0163605 A1 | 6/2014 | VanTassel et al. |
| 2014/0172004 A1 | 6/2014 | De Canniere |
| 2014/0172005 A1 | 6/2014 | De Cannier |
| 2014/0207169 A1 | 7/2014 | Miles et al. |
| 2014/0214074 A1 | 7/2014 | Wheeler et al. |
| 2014/0228733 A1 | 8/2014 | Martinez et al. |
| 2014/0228877 A1 | 8/2014 | Kassab et al. |
| 2014/0257320 A1 | 9/2014 | Fitz |
| 2014/0257365 A1 | 9/2014 | McGuckin, Jr. |
| 2014/0276985 A1 | 9/2014 | Clark et al. |
| 2014/0277074 A1 | 9/2014 | Kaplan et al. |
| 2014/0277117 A1 | 9/2014 | Miles et al. |
| 2014/0288480 A1 | 9/2014 | Zimmerman et al. |
| 2014/0303651 A1 | 10/2014 | Ibrahim et al. |
| 2014/0303721 A1 | 10/2014 | Fung et al. |
| 2014/0330306 A1 | 11/2014 | Kassab |
| 2014/0336676 A1 | 11/2014 | Pong et al. |
| 2014/0336699 A1 | 11/2014 | van der Burg et al. |
| 2014/0343594 A1 | 11/2014 | Miles et al. |
| 2014/0350592 A1 | 11/2014 | Kreidler et al. |
| 2014/0364941 A1 | 12/2014 | Edmiston et al. |
| 2014/0371741 A1 | 12/2014 | Longoria et al. |
| 2014/0379020 A1 | 12/2014 | Campbell et al. |
| 2014/0379021 A1 | 12/2014 | Krishnan |
| 2015/0005704 A1 | 1/2015 | Heisel et al. |
| 2015/0005811 A1 | 1/2015 | Lubock et al. |
| 2015/0039021 A1 | 2/2015 | Khairkhahan et al. |
| 2015/0066074 A1 | 3/2015 | Miles et al. |
| 2015/0119884 A1 | 4/2015 | Fung et al. |
| 2015/0133989 A1 | 5/2015 | Lubook et al. |
| 2015/0157328 A1 | 6/2015 | Miller et al. |
| 2015/0190135 A1 | 7/2015 | Ibrahim et al. |
| 2015/0196305 A1 | 7/2015 | Meyer et al. |
| 2015/0223820 A1 | 8/2015 | Olson et al. |
| 2015/0250482 A1 | 9/2015 | Slaughter et al. |
| 2015/0328026 A1 | 11/2015 | Zimmerman et al. |
| 2015/0342612 A1 | 12/2015 | Wu et al. |
| 2015/0374491 A1 | 12/2015 | Kreidler |
| 2016/0008061 A1 | 1/2016 | Fung et al. |
| 2016/0022273 A1 | 1/2016 | Kassab |
| 2016/0051358 A1 | 2/2016 | Sutton et al. |
| 2016/0058539 A1 | 3/2016 | VanTassel et al. |
| 2016/0066922 A1 | 3/2016 | Bridgeman et al. |
| 2016/0066923 A1 | 3/2016 | Krishnan |
| 2016/0066974 A1 | 3/2016 | Coulombe |
| 2016/0066991 A1 | 3/2016 | Krishnan |
| 2016/0074043 A1 | 3/2016 | Friedman et al. |
| 2016/0095603 A1 | 4/2016 | McGuckin, Jr. et al. |
| 2016/0100844 A1 | 4/2016 | Li et al. |
| 2016/0106437 A1 | 4/2016 | van der Burg et al. |
| 2016/0166242 A1 | 6/2016 | Krishnan |
| 2016/0235412 A1 | 8/2016 | Liddicoat et al. |
| 2016/0262767 A1 | 9/2016 | Miles et al. |
| 2016/0270784 A1 | 9/2016 | Wheeler et al. |

FOREIGN PATENT DOCUMENTS

| | | |
|---|---|---|
| WO | 2009/106907 A1 | 9/2009 |
| WO | 2012/003317 A1 | 1/2012 |

\* cited by examiner

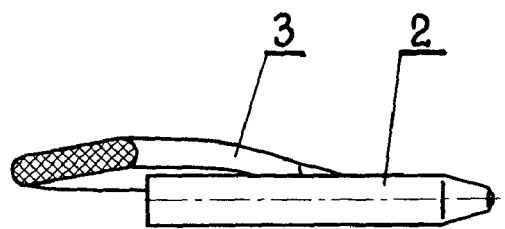
Fig. 5
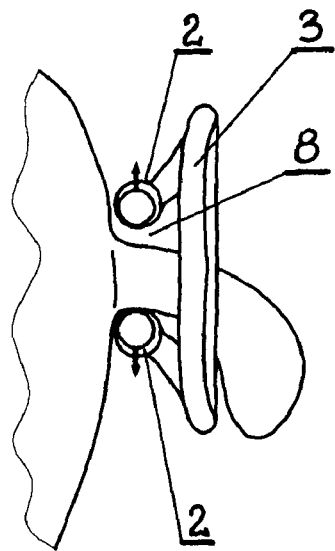 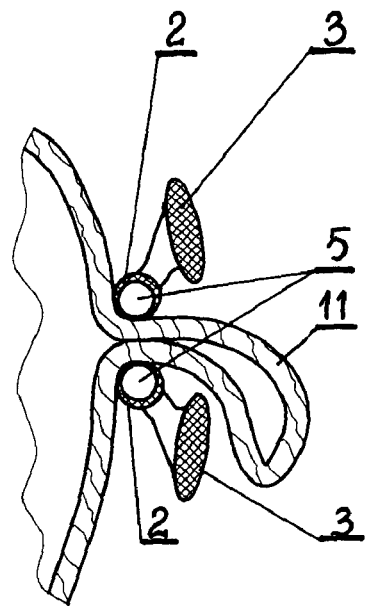
Fig. 6  Fig. 7

LEFT ATRIAL APPENDAGE OCCLUSION DEVICE

CROSS REFERENCE TO RELATED APPLICATIONS

The present application is a § 371 National Phase application based on PCT/PL2014/000031 filed Mar. 31, 2014, the subject matter of which is incorporated by reference in its entirety.

FIELD OF THE INVENTION

The present invention relates to an occlusion device intended for medical use, for occluding the left atrial appendage, constituting an implant. The occlusion device can be used in medicine also for other purposes.

BACKGROUND OF THE INVENTION

The left atrial appendage is a dead end in the blood flow through the heart, but during systole it is filled with blood. As compared to the right atrial appendage, it is longer, thinner and has more undulating surface. From the medical point of view, this organ does not have any significant role. In the case of atrial fibrillation, the left atrial appendage is insufficiently washed by blood, which results in the congestion of the blood. Congestion may cause activation of the coagulation system and formation of blood clots. Blood clots from the inside of the appendage can be released to the cardiovascular system and transferred to important vital structures. Therefore, a frequent complication of atrial fibrillation is an ischemic stroke of the organ perfused by blood containing clots, in the worst case, a cerebrovascular accident. Atrial fibrillation affects about 1% to 2% of the adult population, and every tenth patient over 80. It increases the risk of stroke by five times, while every fifth stroke is associated with this cardiac arrhythmia. Ischemic strokes associated with atrial fibrillation are more often fatal, and patients who survive are often disabled and more often exposed to repeated episodes than patients after strokes caused by any other reason. As a consequence, the risk of death after a stroke due to atrial fibrillation is doubled, and the cost of treatment is 1.5 times higher.

Known solutions aimed at stopping the blood flow through the lumen of the left atrial appendage can be divided into two groups. The first group of solutions aims at closing the blood supply from the inside. The second group of solutions aims at closing the blood supply from the outside by occluding the appendage using an occlusion device from the outside, at the base of the appendage.

A known solution belonging to the first group of solutions is disclosed in U.S. Pat. No. 6,652,555, expressly incorporated herein by reference. This known solution proposes a number of solutions employing a membrane for blocking passage of clots from the inside of the left atrial appendage to the inside of the left atrium. The membrane, secured inside, over, or around the ostium prevents blood clots from escaping from the appendage to the lumen of the left atrium. The membrane may be designed as permeable or impermeable with respect to blood flow, but in either case, stopping blood clots. The membrane is configured to extend over the ostium of the left atrial appendage; therefore, it has an outer periphery with a larger dimension than a dimension of the ostium. According to some embodiments, securing elements are designed so that the membrane has a central mandrel on which an element with self-expanding arms is inserted to the interior of the appendage, what makes it possible, in the next step, to occlude the ostium of the appendage between the membrane and the arms of the element located from the interior of the appendage, when they have been opened.

In another solution, known from US patent specification No. US 2005/0113861, expressly incorporated herein by reference, a different solution is disclosed. According to this known solution, a device comprises a center post and a sheet, stretched over a plurality of ribs, blocking the outflow of blood clots from the left atrial appendage. The sheet stretches over the ribs like a parachute, where from the interior of the appendage there is an open space left, whereas from the left atrium the flow of blood is closed by the sheet.

Another solution belonging to the first group of solutions, known from US patent specification No. US 2006/0247680, expressly incorporated herein by reference, discloses a method and an implantable flange for occluding the blood orifice from the atrium to an appendage. The flange is secured in the lumen of the left atrial appendage, near the orifice, and contains a bigger plate on the atrium side, with a resistance flange and a second plate secured to the flange on a cylindrical wall from the inside of the left atrial appendage. The flange, both plates and the cylindrical wall are semi-flexible. Both plates can be tightened to each other using a screw mechanism, causing the cylindrical wall to bulge radially outward and the flange to be fixed in the orifice of the left atrial appendage.

Another solution belonging to the first group of solutions, known from U.S. Pat. No. 8,828,051, expressly incorporated herein by reference, discloses another device for occluding the interior of the left atrial appendage. The occlusion device comprises a kind of an occluder in the form of a disk configured to prevent blood flow to the left atrial appendage. The occluder, according to this known solution, comprises a main flange, blocking blood supply to the appendage from the left atrium and an auxiliary anchoring flange connected thereto via a flexible connector. The auxiliary flange inserted into the appendage opens up, preventing the whole from prolapsing into the atrium. Coils of the flexible connector are connected with the occluder disk, where the connector has a substantially constant cross-section and allows for variable length, variable orientation, as well as it being bent according to the appendage position. The anchoring flange is inserted in a coiled configuration into the atrium and it contains a shaped edge in the form of an umbrella, preventing prolapsing from the left atrial appendage.

As their design indicates, devices belonging to the first group of solutions need to be arranged in the ostium of the left atrial appendage only from the interior of the left atrium.

Solutions belonging to the second group are external occlusion devices placed at the base of left atrial appendage, without surgical intervention providing access to the inside of the heart. This is usually performed during a surgery by applying an occlusion device on the appendage stalk, which constricts and occludes internal surface of the orifice. This type of an occlusion device must meet stringent requirements. In addition to material requirements as to interaction with body fluids, the pressure force of arms must be constant and must be within strictly defined limits.

Too weak pressure of arms may not be able to stop blood flow to a left atrial appendage and blood outflow from a left atrial appendage. Limiting blood flow only by a partial occlusion of the flow may cause increased formation of blood clots, which may lead to an increased risk of a stroke.

However, too strong pressure of the occlusion device arms may cause necrosis. This means that the pressure force of arms must be within strictly defined limits.

A known solution belonging to the second group is disclosed in the patent specification of international application No. WO 2009/106907, expressly incorporated herein by reference. This specification discloses a left atrial appendage closure device to be placed external to the appendage. The device, according to this known solution, comprises an annular elastic band for medical applications, particularly made of medical silicone or a polymer containing medical silicone. First, the band is enlarged, and after positioning the enlarged band from the outside at the base of the appendage, the elastic band is released from enlarging surgical forceps. When released from the forceps, the band returns to its original size, tightening the base of the appendage causing the closure thereof. In another embodiment of the solution according to this known invention, the described device comprises an additional elastic element associated to the annular elastic band, for example a coil spring, or a mesh, made of biocompatible metal alloy.

Another solution, known from the patent specification of US Patent Application No. US 2004/0030335, expressly incorporated herein by reference, discloses a device and method of use for occluding animal or human tissues. According to this known solution, a clamping ring is disposed on the left atrial appendage. In the first stage, a cover fixed at the end of an arm of a device supplying a gas medium is placed on the appendage from the outside. The clamping ring for clamping the appendage at the base is fixed on the cover. After placing the cover on the appendage, the clamping ring is slid off the left atrial appendage, and the cover is filled with air, which reduces the volume of the appendage, which facilitates clamping of the clamping ring and facilitates removal of the cover from the appendage.

A further known solution from the second group is disclosed in U.S. Pat. No. 8,647,367, expressly incorporated herein by reference, which discloses devices, systems and methods for occlusion of the left atrial appendage. According to this known solution, in the first stage a concentric tube of the device is inserted from the left atrium, wherein an outer jacket allows the inflation of a balloon sealing off blood flow to the appendage, whereas an inner tube is used to aspirate the interior of the appendage. After performing these steps, an outer closure device in the form of a loop is placed at the basis of the appendage.

A different known device belonging to the second group of solutions has been in use. It has the form of an elastic element made of titanium alloy wire with a shape memory, cooperating with a body composed of titanium tubes lined with polyurethane foam lining, wherein the whole is trimmed with polyester knitted fabric. The position of a frame of the device kept in a stretched position by means of threads is rearranged to perpendicular after putting the device through a cannula between ribs. Then, the device is placed on a left atrial appendage, and the threads releasing a spring are cut off, leading to the occlusion of the lumen by the spring, at the base of the left atrial appendage.

However, in most of the solutions belonging to the second group, where surgical intervention inside the heart is not required, it is necessary to lead the entire length of an appendage through the device and only then it is possible to place an occlusion device at the base of the appendage.

Another known solution is disclosed in US patent specification No. US 2008/0039879. This known solution discloses a number of embodiments of an occlusion device, including several variants of clips and springs occluded on an appendage.

SUMMARY AND OBJECTS OF THE INVENTION

The invention aims at developing a new design of an appendage occlusion device, belonging to the second group of solutions, but not requiring leading the whole appendage through the closure device before implantation.

According to the invention, a left atrial appendage occlusion device comprises at least two clamping jaws fixed to a common resilient element. The resilient element holds the jaws close to each other. The resilient element comprises a bow.

The occlusion device of the present invention is characterised in that the bow has the form of a flange with a cut slot. Each of the edges of the slot cut in the flange is connected with the clamping jaw. Each of the clamping jaws contains an internal channel.

In a preferred embodiment according to the present invention, each of the clamping jaws may have the form of a tube.

In the resting position, the clamping jaws maintain a resilient position next to each other. A slot is provided between the clamping jaws in the position of rest, but the slot cannot be wider than the total aggregate thickness of both walls of the left atrial appendage.

In a section perpendicular to the symmetry axes of the internal channels of the clamping jaws, a section of the jaws and a section of the bow arms is visible. In a preferred embodiment of the invention, in this section, an imaginary line connecting the symmetry axes of the internal channels of the clamping jaws is distant from an imaginary line connecting the centres of sections of the bow arms. The imaginary lines do not overlap.

The bow has the shape of a substantially flat or slightly curved flange. The bow according to the invention has in the central part of its periphery a larger section than in the places of connection with the clamping jaws. As a result, the bow strains resiliently when the clamping jaws open up, especially in the area of the jaws, but not in the central part of the bow. The slot being created between the clamping jaws which are resiliently opened up is, owing to this design of the bow, of equal width over the entire length of the jaws. This means that the same working pressure is applied over the entire length of the jaws.

As mentioned above, each clamping jaw contains an internal channel. The clamping jaw wall separates the internal channel from the outer surface of the clamping jaw. According to the invention, the wall of each of the clamping jaws, over the length corresponding to the length of the internal channel, is in its cross-section preferably irregular in thickness. If a clamping jaw is a tube, this means that the cylindrical outer surface of the tube and the cylindrical surface of the internal channel of the tube are not coaxial. The clamping jaw wall from the adjacent clamping jaw side, this in the working area of the clamping jaw, is the thinnest, whereas the wall of the same clamping jaw from the side of connection of the jaw with the bow arm is the thickest.

In a preferred embodiment of the invention, the clamping jaws have straight symmetry axes, so they are straight in shape. However, a different shape of both jaws is not excluded in other embodiments, for example arcuate-shaped jaws.

The ends of the channels in the clamping jaws, from the bow side are open, and from the other side the ends of the channels in the clamping jaws contain closures.

The closures of the internal channels in both clamping jaws, from the opposite side to the bow, in a preferred embodiment of the invention, have the shape of cones. The tops of both cones are preferably turned outwards from each other.

According to the invention it is proposed that two clamping jaws are connected by means of a resilient bow. The jaws from the side of the bow have internal channels open, and from the opposite side, the channels comprise closures in the form of cones, where the tops of the cones are turned outwards. This makes it possible to insert two arms of a device to the internal channels of both jaws, from the side of the bow and open the jaws up using the device, enlarging a slot between the jaws. To the created slot, from the side of the conical closures of both jaws, it is easy to insert the base of the left atrial appendage and after releasing the device, clamp the jaws on the left atrial appendage, owing to the resilient qualities of the bow. The appendage closure is achieved with a single decided movement, without the need to intervene inside the left atrium and thread the whole appendage through the occlusion device loop, as provided for in a number of known solutions. The high speed of cutting-off of the interior of the left atrial appendage from the blood flow into the left atrium, without it being deformed, reduces the risk of blood clots getting into the circulatory system compared to solutions where the left atrial appendage needs to be threaded.

Each of the clamping jaws has an internal channel non-coaxial in relation to the outer wall of the jaw. This is particularly visible when the clamping jaws have the form of tubes. The cylindrical outer surface of a tube has a different symmetry axis here than a cylindrical internal channel. Therefore, the thickness of the tube wall of which each jaw is made is not the same on the periphery. The jaw wall is the thinnest from the side of the other clamping jaw and the thickest from the side of connection with the bow arm. Thus, the small wall thickness of each jaw from the side of the other clamping jaw, so from the side of contact with the left atrial appendage, additionally allows the correction of the pressure of both jaws on the appendage through the bending of the thin wall. Through the straining of the thin part of the wall under the mutual pressure of the jaw and the appendage, the width of contact increases and the highest value of pressure decreases, which is conducive to tissue viability in the area of contact. However, the thicker wall of both jaws from the side of connection with the bow arms prevents the straining of these parts of the surface of the clamping jaws under the pressure of the bow arms.

The bow can be a flat flange but in a preferred embodiment it is arched, thus it better adapts to the shape of the outer layer of the left atrium. The sectional dimension of the bow in a plane parallel to the surface of the left atrium is a few times bigger than the dimension in a direction perpendicular to the surface, which increases the contribution of twisting to the straining of the bow, and reduces bending. A large contribution of twisting makes it possible to preserve parallelism of the jaws when they open up and obtain equal distribution of pressure over the length of their contact with the appendage. In addition, in sections perpendicular to the axes of tubes, the axis passing through the centres of tubes is distant from the axis passing through the centres of the bow sections. This distance comprises the bow twisting arm. When the occlusion device is widened, so when the slot between the jaws is increased, the distance is increased, thus the occlusion device's stiffness is degressive and facilitates placing the occlusion device and reduces the influence of the appendage thickness on the clamping force.

Uniform pressure of both clamping jaws over the length of contact with the left atrial appendage makes it possible to achieve the effect of adhesion of the appendage walls, preventing unfavourable phenomena such as necrosis in the case of too strong a pressure of the clamping jaws.

BRIEF DESCRIPTION OF THE DRAWINGS

The objects of the invention are shown in the embodiment in the accompanying drawings in which individual figures show:

FIG. 5 shows Section A-A of the occlusion device according to FIG. 2.

FIG. 6 shows the occlusion device with the jaws open, when placed on the left atrial appendage.

FIG. 7 shows a section of the occlusion device according to FIG. 9, on the left atrial appendage.

DETAILED DESCRIPTION OF THE PREFERRED EMBODIMENTS

As shown in the embodiment in the accompanying drawings, an occlusion device 1 comprises two clamping jaws 2 fixed to a common resilient element. The resilient element holds the jaws 2 close to each other. The occlusion device 1 is made as a monolithic product, of plastic material inert to the human body, for example of polyamide. The occlusion device can be made using different technologies, but in this embodiment, 3-D printing technology is used.

Figure 1:
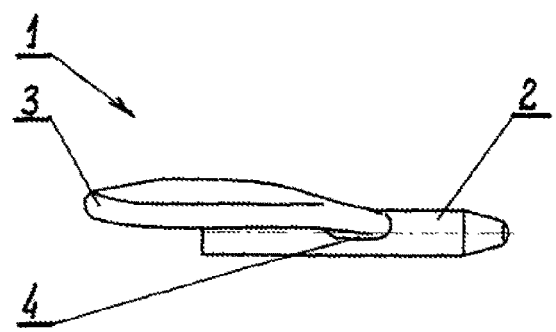
FIG. 1 shows a side view of the occlusion device.

The resilient element comprises a bow 3 in the form of a flange with a cut slot. The slot is not shown in the accompanying drawings, because each of its edges 4 is connected with the clamping jaw 2. The edge 4 of the slot is schematically marked in FIG. 1 and FIG. 2.

Figure 2:
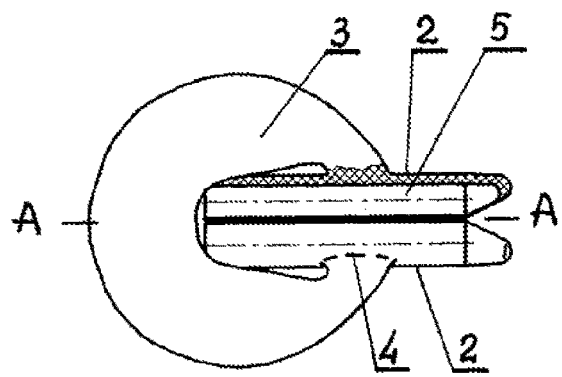
FIG. 2 shows a top view of the occlusion device according to FIG. 1.
Figure 3:
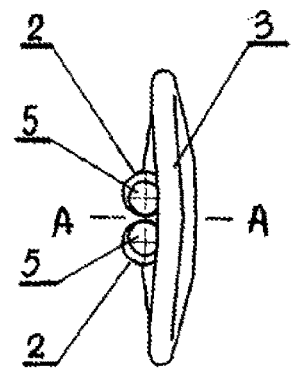
FIG. 3 shows a view of the occlusion device according to FIG. 1 from the direction of the symmetry axes of the channels of the clamping jaws.
Figure 4:
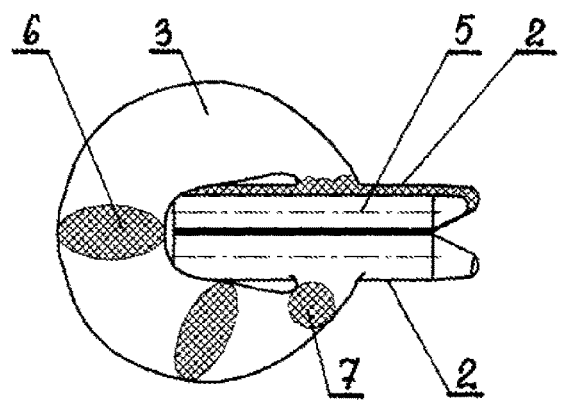
FIG. 4 shows the occlusion device according to FIG. 2 with sections of the bow arms.

Each of the clamping jaws 2 contains an internal channel 5. The clamping jaw 5 in this embodiment of the occlusion device according to the invention has the form of a tube. In other embodiments the clamping jaw 2 may have a different form, for example a flat with rounded edges, comprising the internal channel 5. In the restring position, the clamping jaws 2 maintain a resilient position next to each other. This is shown in FIG. 2, FIG. 3 and FIG. 4. However, a slot is provided between the clamping jaws 2 in the resting position, but the slot cannot be wider than the total thickness of both walls of the left atrial appendage when held together.

FIG. 5 shows the occlusion device according to the invention in Section A-A as shown in FIG. 2.

Figure 8:
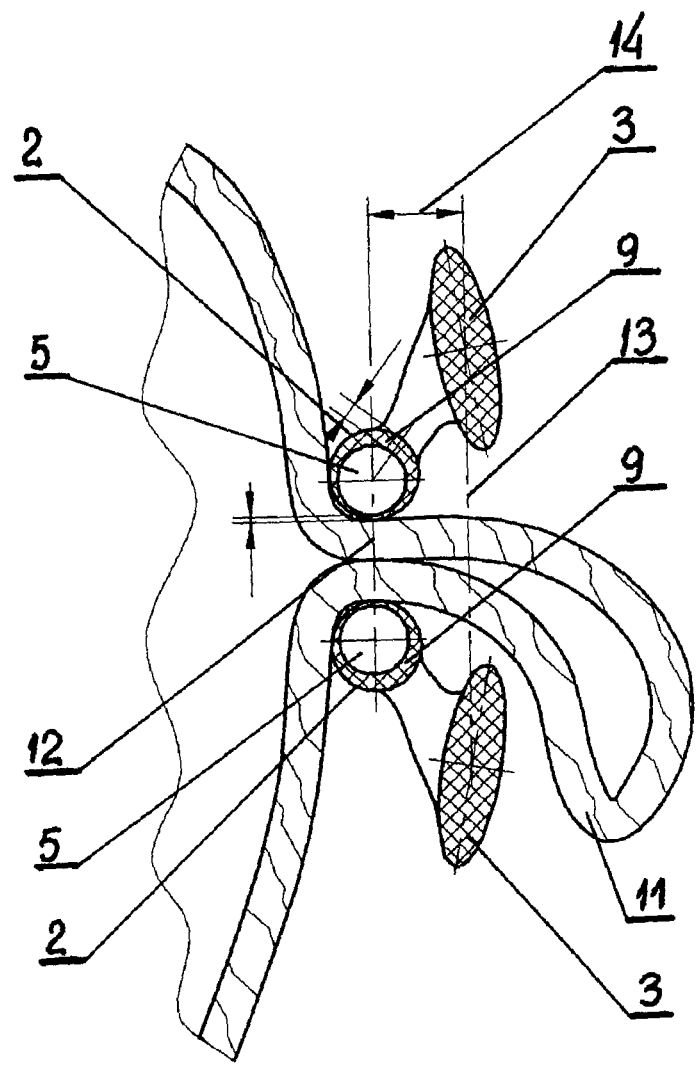
FIG. 8 shows a section of the occlusion device according to FIG. 7 in an enlarged view.

The occlusion device according to the invention is shown in FIG. 7 and FIG. 8 in a section perpendicular to the symmetry axes of the internal channels 5 of the clamping jaws 2. The figures show a section of the jaws 2 and a section of the bow 3 arms.

The embodiment in FIG. 8 shows an enlarged view of a section of the occlusion device with a plane perpendicular to the symmetry axes of the channels 5 in the jaws 2. An imaginary line 12 connecting the symmetry axes of the internal channels 5 of the clamping jaws is shown. The imaginary line 12 is distant from an imaginary line 13 connecting the centres of sections of the bow 3 arms, in this section of the occlusion device 1 by a distance 14.

The bow 3 has the shape of a substantially flat or slightly curved flange. This is shown in FIG. 1, FIG. 2, FIG. 3, FIG. 4, FIG. 5 and FIG. 6. The bow 3 in this embodiment has in the central part of its periphery a larger section 6 than a section 7 near the places of connection with the clamping jaws 2. This is shown in detail in FIG. 4. The same figure also shows an intermediate section of the bow 3 arm between the sections 6, 7. With such changes of the sections a uniform durability of the bow is obtained, but also by reducing a dimension in the section 7, the bending stiffness of the fixing of the jaws to the bow is reduced. As a result, the fixing becomes a resilient joint, equalizing pressure over the length of contact of the jaws and the appendage.

In this embodiment, each clamping jaw 2 has the form of a tube and contains the internal channel 5. In other embodiments of the occlusion device according to the invention the jaws 2 may have a different form, but also each of them preferably comprises the internal channel 5.

The clamping jaw 2 wall 9 separates the internal channel 5 from the outer surface of the jaw 2. In this embodiment of the occlusion device, the wall 9 of each of the clamping jaws 2, over the length corresponding to the length of the internal channel 5, is in its cross-section irregular in thickness. This is particularly clearly shown in FIG. 7 and FIG. 8, and also in FIG. 2, FIG. 3, FIG. 4 and FIG. 6. These figures show that the outer surface and the surface of the internal channel 5 of the jaw 2 are not coaxial. The jaw 2 wall 9 from the adjacent jaw 2 side, in the working area of the clamping jaws 2, is the thinnest, whereas the wall 9 of the same clamping jaw 2 from the side of connection of the jaw 2 with the bow 3 arm is the thickest. The result is a rigid connection of the bow 3 with the jaw 2 from one side of the jaw 2 periphery, and on the other side of the jaw 2 periphery, the wall 9 has some degree of flexibility. The flexible parts of the walls 9 of both jaws 2 face each other. This is shown in detail in FIG. 8.

In the embodiment shown in the accompanying drawings, the clamping jaws 2 comprise tubes and have straight symmetrical axes, so they are straight in shape. However, a different shape of both jaws is not excluded in other embodiments, for example arcuate-shaped jaws. Both jaws 2 have substantially the same shape of the working part. However, in other embodiments they can have different shapes, for example complementary shapes of working surfaces.

FIG. 1, FIG. 2, FIG. 4 and FIG. 5 show that the ends of the channels 5 in the clamping jaws 2, from the bow 3 side are open, and from the other side the ends of the channels 5 in the clamping jaws 2 contain closures 10. The closures 10 of the channels 5 of both clamping jaws 2, from the opposite side to the bow 3, in this embodiment, have the shape of cones. The tops of cones of both closures 10 are turned outwards from each other. This is clearly shown in FIG. 2 and FIG. 4. This turning of the tops of the closures 10 facilitates insertion of the left atrial appendage between the open jaws 2. In other embodiments of the occlusion device according to the invention, the closures 10 may have a different shape.

Figure 9:
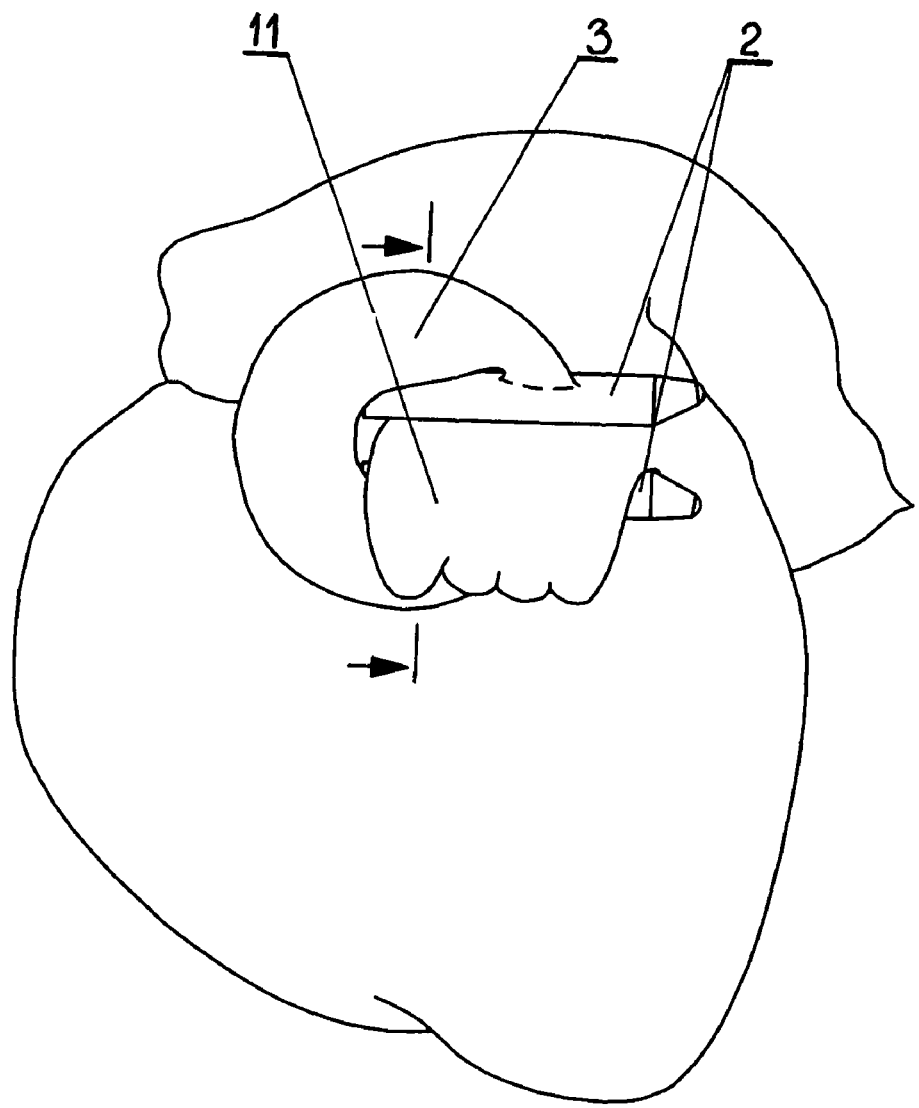
FIG. 9 shows a schematic view of the occlusion device in a working position.

The occlusion device 1 according to the invention is shown in a working position in FIG. 9. The clamping jaws 2 are clamped at the base of the left atrial appendage 11. The occlusion device 1 comprises an implanted implant which after some time results in the adhesion of the appendage 11 walls and the closure of its cavity. This makes it possible to occlude the connection of the left atrium with the internal cavity of the appendage 11 and thus eliminate the place of potential formation and accumulation of dangerous blood clots.

LIST OF DESIGNATIONS IN THE FIGURES

1. Occlusion device.
2. Clamping jaw.
3. Bow.
4. Edge of the bow slot.
5. Internal channel.
6. Section of the central part of the bow.
7. Section of the bow near the jaw 2.
8. Slot between the jaws.
9. Clamping jaw wall.
10. Internal channel closure.
11. Left atrial appendage.
12. Line connecting the symmetry axes of the channels 5.
13. Line connecting the centres of sections of the bow arms.
14. Distance of line 12 from line 13.

What is claimed is:

1. A left atrial appendage occlusion device comprising:
   at least two clamping jaws, each of the clamping jaws having a tubular configuration with an internal channel;
   a common resilient and monolithic bow providing at least two arms connected to the at least two clamping jaws, and being configured to hold the clamping jaws close and next to each other, the bow comprising a flange with a cut slot having edges,
   wherein each of the edges of the cut slot is connected to a respective clamping jaw of the at least two clamping jaws.

2. The left atrial occlusion device according to claim 1, wherein the respective internal channels of the at least two clamping jaws each have an axis of symmetry, and in a section of the bow arms perpendicular to the respective axis of symmetry, an imaginary line connecting the respective axes of symmetry, is distant from an imaginary line connecting the respective center of the sections of the bow arms by a distance.

3. The left atrial occlusion device according to claim 2, wherein the bow has in a central part of its periphery a larger section than a section in where the bow arms are connected with the clamping jaws.

4. The left atrial occlusion device according to claim 1, wherein each of the clamping jaws has a respective wall within the internal channel having, in its cross-section, an irregular thickness, wherein the wall proximate to an adjacent clamping jaw side is the thinnest, and the wall from a side of the clamping jaw connected to the respective bow arm is the thickest.

5. The left atrial occlusion device according to claim 1, wherein the internal channels of the clamping jaws have straight axis of symmetry.

6. A left atrial appendage occlusion device comprising:
   at least two clamping jaws, each comprising an internal channel;
   a common resilient bow providing at least two arms connected to the at least two clamping jaws, and being configured to hold the clamping jaws close and next to each other, the bow comprising a flange with a cut slot having edges,
   wherein each of the edges of the cut slot is connected to a respective clamping jaw of the at least two clamping jaws, wherein the internal channels of the clamping jaws are open from a side connected to the respective bow arm, and are closed on a side opposite to the respective bow arm, and wherein the side of the internal channel of a clamping jaw opposite to the respective bow has a closure having a conical shape, where tips of the conical shapes are divergent from each other.

7. A left atrial appendage occlusion device comprising:

at least two clamping jaws, each comprising an internal channel;

a common resilient bow providing at least two arms connected to the at least two clamping jaws, and being configured to hold the clamping jaws close and next to each other, the bow comprising a flange with a cut slot having edges, wherein each of the edges of the cut slot is connected to a respective clamping jaw of the at least two clamping jaws, and wherein the respective internal channels of the at least two clamping jaws each have an axis of symmetry, and, in a section of the bow arms perpendicular to the respective axis of symmetry, an imaginary line connecting the respective axes of symmetry is distant from an imaginary line connecting the respective center of the sections of the bow arms by a distance.

8. The left atrial occlusion device according to claim 7, wherein the bow has in a central part of its periphery a larger section than a section in where the bow arms are connected with the clamping jaws.

* * * * *